United States Patent [19]

Mize

[11] Patent Number: 5,055,594

[45] Date of Patent: Oct. 8, 1991

[54] FLUOROGENIC TRYPOTOPHANASE SUBSTRATES

[75] Inventor: Patrick D. Mize, Durham, N.C.

[73] Assignee: Becton, Dickinson and Company, Franklin Lakes, N.J.

[21] Appl. No.: 554,506

[22] Filed: Jul. 19, 1990

[51] Int. Cl.$^5$ ............... C07D 311/90; C07D 311/16
[52] U.S. Cl. .................. 549/223; 549/224; 549/225; 549/227; 549/288; 560/100; 562/490; 564/196; 564/204; 435/7.72
[58] Field of Search ............... 549/223, 224, 225, 227, 549/288; 560/100; 562/490; 564/196, 204; 435/7.72

[56] References Cited

U.S. PATENT DOCUMENTS

| | | | |
|---|---|---|---|
| 3,261,827 | 7/1966 | Boresch et al. | 549/227 |
| 3,880,934 | 4/1975 | Rammler | 435/7.72 |
| 4,215,047 | 7/1980 | Sakakibara | 549/288 |
| 4,237,047 | 12/1980 | Sakakibara | 549/288 |
| 4,259,233 | 3/1981 | Carrico et al. | 435/7.72 |
| 4,318,980 | 3/1982 | Bogurlaski et al. | 435/7.72 |
| 4,476,229 | 10/1984 | Fino et al. | 549/223 |
| 4,557,862 | 12/1985 | Mangel et al. | 549/227 |
| 4,603,108 | 7/1986 | Bascomb | 435/34 |
| 4,777,269 | 10/1988 | Scheper et al. | 549/288 |

FOREIGN PATENT DOCUMENTS

| | | |
|---|---|---|
| 108400 | 5/1984 | European Pat. Off. |
| 53-084974 | 7/1978 | Japan . |
| 53-108974 | 9/1978 | Japan . |

OTHER PUBLICATIONS

Godsey et al., *Journal of Clinical Microbiology*, 13, 483, (1981).
Suelter et al., *Methods in Enzymology*, 82,561 (1979).
Shute et al., *Synthesis*, 1987, 346.

*Primary Examiner*—C. Warren Ivy
*Assistant Examiner*—Ba K. Trinh
*Attorney, Agent, or Firm*—Richard E. Brown

[57] ABSTRACT

A fluorogenic substrate for tryptophanase useful for identifying an unknown microorganism is a fluorescent dye linked to an amino acid by a carbamate or thiocarbamate group. In preferred substrates, the dye is fluorescein or 7-amino-4-methyl coumarin and the amino acid linked thereto is cysteine, threonine or serine.

6 Claims, No Drawings

FLUOROGENIC TRYPOTOPHANASE SUBSTRATES

BACKGROUND OF THE INVENTION

1. Field of the Invention

This invention relates to the identification of microorganisms, and more particularly relates to an enzyme substrate useful in identification of an organism by analysis of its enzyme content.

2. Background

Many disease states are the result of a bacterial invasion of a body tissue or fluid such as blood, urine, cerebrospinal fluid or synovial fluid. Successful treatment of such infections requires early diagnosis, and proper treatment cannot be initiated until accurate identification of the pathogen has been accomplished. This is made difficult in the early stages of the infection because the concentration of the pathogen is low.

Several procedures currently in use in hospital microbiology laboratories for bacterial identification are growth-based methods which generally require 18-24 hours or longer following isolation of an organism to achieve identification. In some situations, this length of time before identification can be life-threatening.

Identification of a pathogen by determination of which enzymes are present has been investigated. This method depends upon hydrolysis of fluorogenic or chromogenic substrates by enzymes expressed by the organism and is generally conducted by inoculating a panel of substrates and correlating the resulting fluorogenic or chromogenic profile with profiles developed with the same panel for known organisms. Representative of this method is the disclosure of Bascomb in U.S. Pat. No. 4,603,108.

Godsey et al., in *Journal of Clinical Microbiology*, 13, 483 (1981), discloses a method and apparatus for profiling enzymes expressed by strains of the family Enterobacteriaceae using fluorogenic substrates from β-methylumbelliferone, β-naphthylamine and 7-amino-4-methyl coumarin (AMC).

Tryptophanase is an enzyme, present in certain bacteria, that catalyzes the conversion of tryptophan to indole, pyruvic acid and ammonia. A substrate, S-(2-nitrophenyl) cysteine, which is cleaved by this enzyme to the chromophore 2-nitrothiophenol has been disclosed by Suelter et al., *Methods in Enzymology* 82, 561, (1979).

There is a need for a fluorogenic substrate for trypotophanase which could be included in enzyme profiling panels for bacterial identification. Such a substrate would greatly improve the accuracy of bacterial identification by this procedure, in particular for species of Enterobacteriaceae. It is toward fulfillment of this need that the present invention is directed.

SUMMARY OF THE INVENTION

A fluorogenic substrate for tryptophanase includes a fluorescent dye moiety and an amino acid moiety in which a nucleophilic group on the dye is linked to a nucleophilic group, other than the α amino group, of the amino acid by a carbonyl or thiocarbonyl group. In preferred substrates, the amino acid is threonine, cysteine, or, most preferably, serine, and the fluorescent dye moiety is fluorescein, rhodamine, β-naphthylamine or, preferably a coumarin derivative. The most preferred dye is AMC.

The preferred substrate of the invention is nonfluorescent itself but is cleaved by tryptophanase to the amino acid and AMC. It may be used to determine whether an unknown microorganism contains tryptophanase, and may be included in a device in which identification of the unknown microorganism is made on the basis of its enzyme content.

Identification of an unknown microorganism by determination of a profile of its enzyme content and comparison with profiles of known organisms is generally accurate for most organisms. The technique, however, is less accurate for Enterobacteriaceae with currently available substrates. Because some species of Enterobacteriaceae express tryptophanase and others do not, inclusion of the substrate of the invention in a profiling device improves the accuracy of identification of this group of microorganisms.

DETAILED DESCRIPTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments described. The scope of the invention will be measured by the appended claims and their equivalents.

Tryptophanase catalyzes the conversion of tryptophan to indole, pyruvic acid and ammonia, and micoorganisms which contain this enzyme are often termed indole positive. Exemplary of indole positive microorganisms are *Escherichia coli, Citrobacter diversus, Proteus vulgaris, Morganella morganii* and *Klebsiella oxytoca*. Representative indole negative organisms are *Klebsiella pneumoniae, Citrobacter freundii* and *Proteus mirabilis*.

Determination of whether an unknown microorganism is indole positive or indole negative is useful in identification of the unknown. In particular, accurate identification of Enterobacteriaceae species is facilitated by determination of an organism's indole classification.

The substrate of the present invention may be used to determine the indole classification of microorganisms in a clinical sample, such as urine, stool, wound, throat, genital samples or normally sterile body samples such as blood, cerebrospinal fluid or synovial fluid. In the present invention, the term microorganisms is contemplated to include any minute organism which produces enzymes, such as molds, yeasts and preferably bacteria.

The fluorogenic tryptophanase substrate of the present invention may be of the structure I:

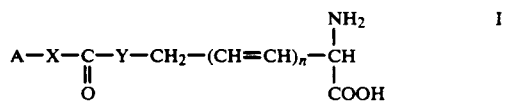

In structure I, A may be a fluorescent dye moiety, X,Y and Z may independently be O,S or NH, and n may be 0-3 Exemplary of suitable fluorescent dye moieties are (1) AMC wherein X is NH;
(2) 7-hydroxy-4-methyl coumarin wherein X is O;
(3) fluorescein, wherein X is O;
(4) rhodamine, wherein X is NH;
(5) β-naphthylamine wherein X is NH.

Preferred substrates of the invention are serine, cysteine and threonine derivatives of fluorescein and AMC in accordance with structure II

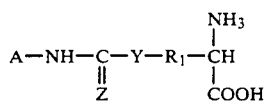

wherein A may be fluorescein or AMC, $R_1$ may be $CH_2$ or $CH_2CH=CH$ and Y and Z may be O or S. In the most preferred substrate, A is 4-methylcoumarin, Y and Z are O and $R_1$ is $CH_2$.

The substrates of the invention may be synthesized from commercially available fluorescent dyes by well-known synthetic routes. In a preferred route, a dye substituted with an amino group may be converted to the corresponding isocyano or isothiocyano derivative and reacted with an appropriately protected amino acid of the structure III

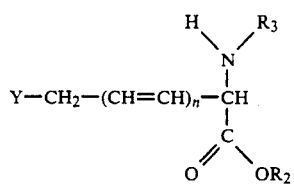

wherein Y may be OH, SH or $NH_2$, n may be 0 to 3 and $R_2$ and $R_3$ are conventional amino acid protecting groups such as carbobenzyloxy, benzyl, lithium and trimethylsilylethoxycarbonyl (Teoc). Preferred protecting groups are lithium as $R_2$ and Teoc as $R_3$ (as described in Example I). It is evident that this synthetic route leads, after removal of the protecting groups, to structure I wherein X is NH and Z is O from an isocyano substituted dye and to structure I wherein X is NH and Z is S from an isothiocyano substituted dye. Thus, for example, a substrate wherein A is rhodamine, X is NH, Z is S, Y is O and $R_1$ is methylene will result from reaction of rhodamine isothiocyanate and a doubly protected serine.

A suitable route for synthesis of a substrate IV wherein X is O is shown in the following equation:

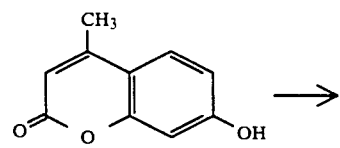

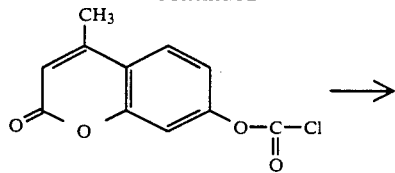

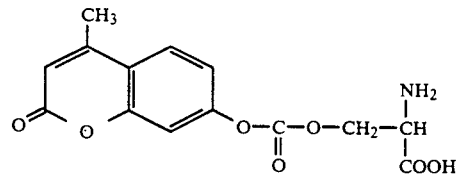

This equation shows conversion of the fluorophore 7-hydroxy-4-methylcoumarin to its chloroformyl derivative and reaction of this intermediate with doubly protected serine to give, after removal of the protecting groups, the tryptophanase substrate IV.

Other routes for synthesis of the tryptophanase substrates of the invention will be evident to those skilled in the art, and a detailed experimental procedure for synthesis of the most preferred substrate, V, is given in Example I.

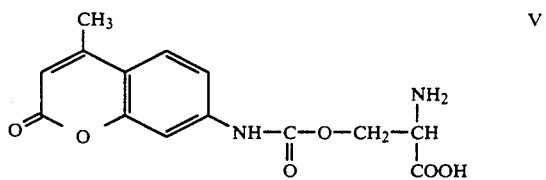

When the substrate of the invention is incubated with an organism which expresses tryptophanase, the fluorogenic substrate, which is not fluorescent itself, is cleaved by the enzyme as shown below to give pyruvic acid, AMC, $CO_2$ and ammonia.

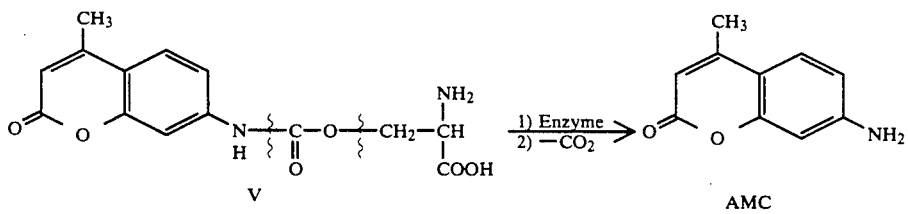

Detection of fluorescence identifies the organism as indole positive. Absence of fluorescence indicates that the organism is indole negative.

The substrate of the invention may be included in a device for identification of an unknown organism. A preferred device in which the substrate of the invention may be used is described in copending Application Ser. No. 209,677 filed on June 20, 1988, of common assignee with the present application, which is herein incorporated by reference.

When used in conjunction with the device of Application Ser. No. 209,677, the substrate of the present invention may be combined with the support disclosed in Application Ser. No. 209,677. The substrate may be contacted with a fluid sample suspected of containing the unknown, preferably after treating the organism with a cell membrane-perturbing reagent, such as a detergent, to enhance release of intracellular enzymes into the fluid sample. If the unknown organism is indole positive, tryptophanase present in the fluid sample reacts with the substrate to release the fluorogen. The absence of fluorescence from the support containing the substrate of the invention identifies the unknown organism as indole negative. Determination of the rate at which the fluorescence develops provides information on the rate of hydrolysis of the substrate and therefore on the concentration of tryptophanase in the organism. The indole reaction of the unknown organism thus determined may be included as part of a profile of the enzyme content of the unknown developed using a plurality of other enzyme substrates deposited on other supports in the device. The profile may then be compared with profiles of known microorganisms developed under substantially the same assay conditions, and the unknown may be identified by the profile of the known microorganism which is closest to that of the unknown.

The tryptophanase substrate of the invention may also be used in conjunction with the device of Application Ser. No. 209,677 for identification of an unknown organism by determining its susceptibility profile to a range of antibiotics. Each of a plurality of the supports of Ser. No. 209,677 may contain the substrate of the invention and a different antibiotic. The supports may be inoculated with the unknown organism in a liquid growth medium and incubated. If the antibiotic is effective against the unknown, growth is inhibited, enzyme is not produced, the substrate is not hydrolyzed and fluorescence does not develop. If the antibiotic is ineffective, the unknown organism grows and expresses the enzyme which hydrolyzes the substrate and causes fluorescence. As described above, information obtained using the tryptophanase substrate of the invention may be combined with information obtained by using substrates for other enzymes to develop a profile of the reactivity of the unknown toward various antibiotics. The susceptibility profile of the unknown may be compared with profiles of known organisms for identification.

The substrates of the invention may also be used with the device of Ser. No. 209,677 to determine the minimum inhibitory concentration (MIC) of various antibiotics toward the unknown. For this application, a panel of supports contains a range of concentrations of the antibiotics and the substrate of the invention. After inoculation and incubation, the effectiveness of the antibiotic concentration on each support is given by the level of fluorescence. Those supports having a minimum level of fluorescence above a control value from an uninoculated support gives the MIC of the antibiotic against the unknown organism.

The following examples are provided to further describe the invention but are not to be considered as limitative of the invention.

ROUTINE ANALYTICAL TECHNIQUES

Analytical TLC was performed on 0.25 mm, 5 cm×20 cm aluminum-backed silica gel plates (catalog number 5534) from EM Science (Cherry Hill, N.J.). Analytical reverse phase HPLC was performed on a Waters 860 two pump system with photo diode array detection (200 to 600 nm) using a Waters Delta Pak C-18 100 A, 4.6×220 mm column (SN-338B31162); Conditions used were: initial hold for 60 minutes at 0.2% trifluoroacetic acid in water followed by a linear radient to 0.2% trifluoroacetic acid in THF over a 1 hour period. Melting points were obtained with a Thomas Hoover capillary melting point apparatus (Philadelphia, Pa.) and are uncorrected. Fluorescence spectra were recorded on a Perkin Elmer LS-5 Fluorometer. NMR spectra were recorded on an IBM/Brucker WP-200SY (200 mHz) (Billerica, Mass.). Chemical shifts are reported relative to tetramethyl silane. High resolution mass spectra were performed by D. S. Millington, Mass Spectrometry Facility, P.O. Box 3028, Duke University Medical Center, Durham, N.C. 27710.

EXAMPLE I

Synthesis of Serine AMC Carbamate, (V)

A. Synthesis of 4-methyl-7-isocyanocoumarin

A 200 mL three neck round bottom flask fitted with dry ice condenser and magnetic stirrer was charged with 2.0 ml of a 20% phosgene/toluene solution and 80 ml of dry dioxane. To this mixture was added 2.0 g (0.0114 moles) of solid AMC and the mixture refluxed overnight. The mixture turned from yellow to a precipitated white solid. An additional 7.0 ml of the 20% phosgene/toluene solution was added and the mixture further refluxed for an additional 5 hours at which time the solution cleared. An argon gas inlet tube was added to the flask and argon was bubbled through the solution to remove excess phosgene and traces of HCl. The cloudy mixture was filtered to remove unreacted AMC and concentrated to yield 2.0 g, 87% yield, of a white solid which was the desired product. NMR (CDCl$_3$) ppm: 2.43 (s, 3H), 7.02 (s, 1H), 7.39 (dd, 3H). IR: strong absorbance at 2250 cm$^{-1}$; no absorbance at 3800 to 3500 cm$^{-1}$.

B. Synthesis of N-trimethylsilylethyloxycarbonyl-o-carbonylamino-7-(4-methylcoumarinyl)-L-serine lithium salt A 100 mL three neck round bottom flask fitted with magnetic stirrer was charged with 1.16 (4.16 mmoles) of the lithium salt of N-trimethylsilylethyloxycarbonyl-L-serine (Shute et al., Synthesis 1987, 346) and 20 ml of acetonitrile. To this mixture was added 0.84 g (4.18 mmoles) of 4-methyl-7-isocyanocoumarin (product of A) dissolved in 15 ml of THF. This mixture was stirred at ambient temperature for 48 hours. The mixture was then filtered and yielded 1.32, g of a greenish white solid. The solid was suspended in a saturated solution of sodium hydrosulfate and stirred for a period of 1 hour. The suspension was then filtered and yielded 0.84 g (1.83 mmoles) 44% yield. Fast atom bombardment (FAB) mass spec gave a [MH+Na]$^+$ of 479. NMR (DMSO d6): ppm: 0.0 (bs, 9H), 0.90 (m, 2H), 2.38 (s, 3H), 4.01 (m, 4H), 4.30 (m, 2H), 7.09 (m, 4H), 10.26 (s, 1H). HPLC retention time 98 minutes.

C. Synthesis of serine-AMC-carbamate, V

A 10 mL flask was charged with 2.0 ml of anhydrous trifluoroacetic acid (TFA) and cooled to 0° C. under an atmosphere of argon. To the cooled TFA was added 0.24 g (0.525 mmoles) of the product from B. This solution was stirred for 4 hours at 0° C., concentrated on a rotary evaporator under reduced pressure. The residue was dissolved in methanol, ether was added and a white solid precipitated. This white solid was filtered and yielded 0.178 g (80.9%). Melting point = 185° to 186° C. (decomposition). NMR (CDCl$_3$+CF$_3$COOH): ppm: 2.54 (s, 3H), 4.85 (m, 3H), 6.44 (s, 1H), 7.66 (4H). HPLC retention time 74 minutes. High resolution mass spec [MH+]: $C_{14}H_{15}N_2O_6$. Calculated 307.0848. Found 307.0937

EXAMPLE II

Reaction of Serine-AMC-Carbamate with Tryptophanase

To a $1.19 \times 10^{-6}$M solution of serine-AMC-carbamate dissolved in 100 mM potassium phosphate buffer, pH 8.2 was added 100 μL of a 5.0 mq/mL solution of tryptophanase. Fluorescence increase was measured at 440 nm, with excitation at 365 nm. Starting fluorescence of the serine-AMC-carbamate solution was 26 relative units. After addition of the enzyme, fluorescence at 440 nM increased at a rate of 97 units/minute. This result showed that the enzyme was catalyzing the conversion of serine-AMC carbamate to 7-amino-4-methyl-coumarin. Fluorescence increase in the absence of enzyme was negligible.

EXAMPLE III

Determination of the Indole Reaction of Microorganisms

Aliquots of 20 microliters of a 0.5% solution of the substrate of Example I dissolved in dimethylsulfoxide were added to cellulose disks (catalog no. 740-E, Schleicher and Schuell, Inc. Keene, N.H.). The DMSO was removed by vacuum dessication. The dried disks were placed in the wells of a black polystyrene microwell tray. Four of the disks were each inoculated with 25 microliters of a suspension containing $3 \times 10^8$ colony forming units per ml of the known indole positive microorganisms *Escherichia coli* and *Citrobacter diversus* and the known indole negative microorganisms *Klebsiella pneumoniae* and *Citrobacter freundii*. The suspensions were made in phosphate buffer, pH 8.4, containing toluene at a concentration of 2 drops per 5 ml of buffer to permeabilize the bacteria. Four disks were inoculated with buffer alone to serve as controls. The disks were excited at 365 nm using a xenon lamp and fluorescence was measured at 1 minute intervals for 10 minutes at a wavelength of 440 nm using a Fluoroskan II (Flow Laboratories, McLean, Va. 22102) reader. Results from the four tubes for each organism were averaged and are expressed in the Table as nanograms of free AMC released per minute.

TABLE

| ORGANISM | STRAIN | FLUORESCENCE INCREASE (ng AMC/min) |
| --- | --- | --- |
| E. coli | 1W9901N1 | 1.53 |
| E. coli | 2W0803N1 | 1.85 |
| E. coli | 4H8162N1 | 1.6 |
| E. coli | 7W0563N1 | 1.7 |
| C. diversus | 404 | 5.35 |
| C. diversus | 2075 | 4.4 |

TABLE-continued

| ORGANISM | STRAIN | FLUORESCENCE INCREASE (ng AMC/min) |
| --- | --- | --- |
| K. pneumoniae | 6N3696N1 | 0.5 |
| C. freundii | 2027 | 0.8 |
| C. freundii | 2058 | 0.45 |
| CONTROL | | 0.43 |

It is seen from the Table that indole negative organisms *K. pneumoniae* and *C. freundii* have about the same fluorescence increase as the control whereas the indole positive organisms *E. coli* and *C. diversus* have much larger fluorescence increases due to release of free AMC.

What is claimed is:

1. A fluorogenic tryptophanase substrate of the structure

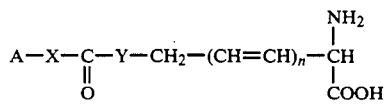

wherein A is a fluorescent dye moiety selected from the group consisting of a coumarin, fluorescein, rhodamine and β-naphthylamine, Y is selected from the group consisting of O and S, X is selected from the group consisting of O and NH and n is 0 to 1.

2. The substrate of claim 1 wherein A is a 4-methyl coumarin moiety.

3. The substrate of claim 2 wherein A—X is a 7-amino-4-methyl coumarin moiety.

4. The substrate of claim 2 wherein A—X is a 7-hydroxy-4-methyl coumarin moiety.

5. A fluorogenic tryptophanase substrate of the structure

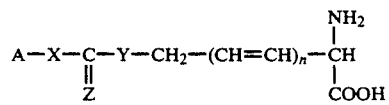

wherein A is a fluorescent dye moiety selected from the group consisting of a coumarin, fluorescein, rhodamine and for naphthylamine, X,Y and Z are independently selected from the group consisting of O,S and NH, and n is 0 to 3.

6. A fluorogenic tryptophanase substrate of the structure

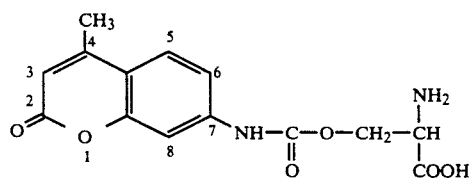

* * * * *